United States Patent [19]

Stoltefuss et al.

[11] Patent Number: 5,571,928
[45] Date of Patent: Nov. 5, 1996

[54] 4-AMINO-3-HYDROXY-PHTHALIMIDINE, AND A PROCESS FOR THE PREPARATION THEREOF

[75] Inventors: Jürgen Stoltefuss, Haan; Michael Negele, Solingen; Friedrich Dürholz, Remscheid, all of Germany

[73] Assignee: Bayer Aktiengesellschaft, Leverkusen, Germany

[21] Appl. No.: 504,380

[22] Filed: Jul. 19, 1995

[30] Foreign Application Priority Data

Jul. 26, 1994 [DE] Germany ............... 44 26 374.0

[51] Int. Cl.⁶ .................................................. C07D 209/48
[52] U.S. Cl. .................................................. 548/481
[58] Field of Search ................................. 548/481

[56] References Cited

U.S. PATENT DOCUMENTS 3,849,438  11/1974  Houlihan et al. ............ 548/481 X

FOREIGN PATENT DOCUMENTS 0452712  10/1991  European Pat. Off. .
0476474   3/1992  European Pat. Off. .

OTHER PUBLICATIONS

T. Watanabe, et al., Chem. Pharm. Bull., vol. 20, No. 10, pp. 2123–2127, (1972).
T. Watanabe, et al., Chem. Pharm. Bull., vol. 26, No. 2, pp. 530–538, (1978).
T. Watanabe, et al., Chemical Abstracts, vol. 85, No. 21, abstract No. 160009t, (1976).
J. March, Advanced Organic Chemistry, 4th Ed., John Wiley & Sons, Inc., New York, pp. 1216–1217, (1992).

*Primary Examiner*—Jacqueline Haley
*Attorney, Agent, or Firm*—Sprung Horn Kramer & Woods

[57] ABSTRACT

The present invention relates to 4-amino-3-hydroxy-phthalimidine, an important intermediate for the synthesis of 3-substituted 5-quinoline-carboxylic acid amides, and a process for the preparation thereof.

5 Claims, No Drawings

4-AMINO-3-HYDROXY-PHTHALIMIDINE, AND A PROCESS FOR THE PREPARATION THEREOF

The present invention relates to 4-amino-3-hydroxy-phthalimidine, an important intermediate for the synthesis of 3-substituted 5-quinoline-carboxylic acid amides, and a process for the preparation thereof.

The publication *J. Chem. Pharm. Bull.* 26, 530–538 (1978) has already disclosed 3-hydroxy-4-nitrophthalimidine.

The present invention provides the new compound 4-amino-3-hydroxyphthalimidine of the formula (I).

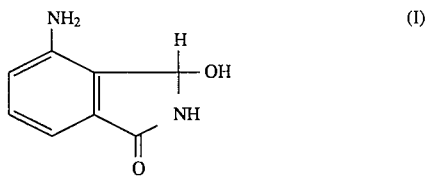

The invention further provides a process for preparing the compound of the formula (I), characterized in that 4-nitro-3-hydroxyphthalimidine of the formula (II)

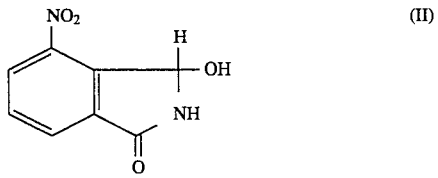

is hydrogenatively reduced in inert solvents in the presence of a catalyst, in solution or in suspension, by conventional methods.

The process can be represented by the following reaction scheme:

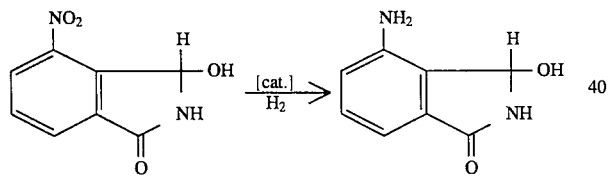

Solvents which are suitable for the hydrogenation are water and all organic solvents which do not change under the reaction conditions. These include alcohols such as methanol, ethanol, propanol or isopropanol, or ethers, such as diethyl ether, dioxane, tetrahydrofuran, glycol dimethyl ether or diethylene glycol dimethyl ether, or amides such as hexamethylphosphoramide or dimethylformamide, or acetic acid, and also methylene chloride, carbon tetrachloride or toluene. It is likewise possible to use mixtures of the specified solvents. It is also possible to use mixtures of, for example, methanol, ethanol, propanol or tetrahydrofuran and their mixtures with water. In this case, preference is given to mixtures of methanol with water.

The hydrogenation can be carried out at atmospheric pressure or at superatmospheric pressure, for example at from 0.5 to 100 bar, preferably at 5–50 bar, particularly preferably 8–12 bar.

Suitable catalysts for the catalytic hydrogenation with hydrogen are, for example, those which consist of metals and/or compounds of elements of transition group VIII of the Periodic Table of the Elements or contain these. Preference is here given to the metals ruthenium, rhodium, palladium, platinum, cobalt and nickel and compounds thereof. Such metals and metal compounds can also be applied to support materials. Metallic catalysts can also be used as skeletal catalysts of the Raney type.

Suitable amounts of catalyst are, for example, from 0.00001 mol to 1 mol, preferably 0.0001 to 0.1 mol, based on 1 mol of the formula (II).

Particular preference is given to palladium catalysts on supports such as Pd/C, Pd/BaSO$_4$, Pd/Al$_2$O$_3$ or Raney nickel.

The optional addition of basic salts has been found to be favourable to the course of the reaction. These salts include alkali metal or alkaline earth metal acetates such as, for example, sodium or potassium acetate, or alkali metal carbonates or alkali metal hydrogen carbonates such as, for example, sodium or potassium carbonate or hydrogen carbonate.

The compound of the formula (II) is known [cf. T. Watanabe et al., *Chem. Pharm. Bull*, 20(10), 2123–2127 (1972)].

The above preparative process can be carried out both in batch mode and semi-continuously.

The above preparative process is given only for clarification. The preparation of the compound of the invention of the formula (I) is not limited to this process.

The compound of the invention is a valuable starting material or intermediate for preparing 3-substituted quinolinealdehydes, which are of importance as precursors for 1,4-dihydropyridines. They can be cyclized to give pharmacologically important dihydropyridine active ingredients, for example using β-ketoesters and enamines.

PREPARATIVE EXAMPLES

EXAMPLE 1

4-Amino-3-hydroxyphthalimidine

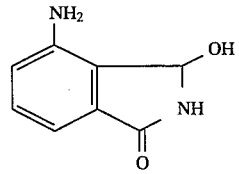

Method A:

20 g (104 mmol) of 3-hydroxy-4-nitro-phthalimidine are dissolved in 1 l of warm methanol and hydrogenated at 3.5 bar using 2.5 g of Pd/BaSO$_4$. During this procedure, the temperature of the reaction rises to 55° C. The reaction is complete after 5 minutes, the mixture is filtered with suction at about 50° C. through Celite and the filter is washed with methanol. The filtrate is evaporated almost to dryness, filtered with suction and the residue washed with cold methanol. This gives 14.6 g (86.5% of theory) of pale yellow crystals having a melting point from 260° C. (decomposition).

The mother liquor gives, by means of evaporation and filtration with suction with ethyl acetate, a further 1.4 g (8.3% of theory) of crystals having a melting point from 260° C. (decomposition).

Method B:

582.4 g (3 mol) of 3-hydroxy-4-nitro-phthalimidine and 37 g of sodium acetate are hydrogenated over 30 g of palladium/carbon (5% palladium) in 3.6 l of methanol in a 10 l (V4A) stainless steel stirred autoclave at about 40° C. and a hydrogen pressure of 6–10 bar. The reaction time is 2 hours. The suspension is finally filtered off, the crude product containing catalyst is dried and processed further.

Yield: 395.7 g (80.3% of theory).

Method C:

582.4 g (3 mol) of 3-hydroxy-4-nitro-phthalimidine are hydrogenated over 30 g of Raney nickel in 3.5 l of methanol in a 10 l (VA) stirred stainless steel autoclave at about 30° C. and a hydrogen pressure of 30 bar. The reaction time is 8 hours. The suspension is filtered off, washed with water and the catalytic crude product is further processed while moist with water.

Yield: 98.5% of theory (according to HPLC; evaluation in % by weight).

Method D:

110 g of 3-hydroxy-4-nitro-phthalimidine (about 87%-pure crude material) are hydrogenated in 600 ml of methanol in a 1.3 l (VA) stainless steel autoclave having an anchor-blade stirrer with the addition of about 5 g (5%) of Pd/carbon and 10 g of $NaHCO_3$. The reaction time is 1 hour. The mixture is then hydrogenated further for 1 hour at constant $H_2$ pressure. The hydrogenation product is very largely dissolved by stirring with 2.3 l of methanol at 60° C. The solution is filtered and evaporated on a rotary evaporator. This gives 76 g (91% of theory) of crystals.

Method E:

Using a method similar to that of variant D, the reaction is carried out at 50 bar of $H_2$ and over 1.7 g (5%) of Pd/carbon with the addition of 20 g of $NaHCO_3$. This gives 73.2 g (88.4% of theory) of a pale yellowish solid product.

We claim:

1. 4-Amino-3-hydroxyphthalimidine of the formula (I)

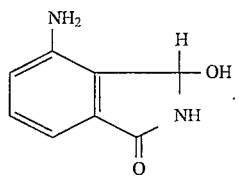

(I)

2. Process for preparing the compound of the formula (I) according to claim 1, wherein 4-nitro-3-hydroxyphthalimidine of the formula (II)

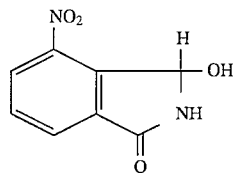

(II)

is hydrogenatively reduced in inert solvents in the presence of a catalyst in solution or in suspension.

3. Process according to claim 2, wherein the hydrogenation is carried out at 0.5–100 bar and optionally in the presence of basic salts.

4. Process according to claim 2, wherein use is made of catalysts applied to support materials.

5. Process according to claim 2, wherein palladium catalysts are used.

* * * * *